United States Patent
Kim et al.

(10) Patent No.: US 8,816,065 B2
(45) Date of Patent: Aug. 26, 2014

(54) PHARMACEUTICAL OR COSMETIC COMPOSITION CONTAINING NICOTINIC ACID ADENINE DINUCLEOTIDE PHOSPHATE OR DERIVATIVE THEREOF

(75) Inventors: Kwang-Nyeon Kim, Yongin-si (KR);
Jung-Min Cho, Bucheon-si (KR);
Joo-Hyun Son, Gumi-si (KR);
Uh-Hyun Kim, Jeonju-si (KR);
Kwang-Hyun Park, Jeonju-si (KR)

(73) Assignee: Damy Chemical Co., Ltd., Seoul (KR)

( * ) Notice: Subject to any disclaimer, the term of this patent is extended or adjusted under 35 U.S.C. 154(b) by 0 days.

(21) Appl. No.: 13/814,956

(22) PCT Filed: Aug. 10, 2011

(86) PCT No.: PCT/KR2011/005848
§ 371 (c)(1),
(2), (4) Date: Feb. 8, 2013

(87) PCT Pub. No.: WO2012/020989
PCT Pub. Date: Feb. 16, 2012

(65) Prior Publication Data
US 2013/0137177 A1 May 30, 2013

(30) Foreign Application Priority Data

Aug. 10, 2010 (KR) .................. 10-2010-0076973

(51) Int. Cl.
| | |
|---|---|
| *A61K 31/7076* | (2006.01) |
| *A61Q 19/08* | (2006.01) |
| *A61K 8/60* | (2006.01) |
| *A61Q 19/00* | (2006.01) |
| *A61K 31/7084* | (2006.01) |

(52) U.S. Cl.
CPC ............ *A61K 31/7076* (2013.01); *A61Q 19/08* (2013.01); *A61K 8/606* (2013.01); *A61Q 19/00* (2013.01); *A61K 31/7084* (2013.01)
USPC ........................................ 536/26.22; 435/377

(58) Field of Classification Search
CPC .......................... A61K 8/606; A61K 31/7076
USPC ........................................ 536/26.22; 435/377
See application file for complete search history.

(56) References Cited

FOREIGN PATENT DOCUMENTS

| | | |
|---|---|---|
| JP | 09-002952 A | 1/1997 |
| JP | 2008-538923 A | 11/2008 |
| KR | 1020090120350 A | 11/2009 |

OTHER PUBLICATIONS

Santella et al. (Journal of Biological Chemistry, vol. 275, No. 12, p. 8301-8306, 2000).*
Churchill et al. (Journal of Biological Chemistry, vol. 275, No. 49, p. 38687-38692, 2000).*

(Continued)

*Primary Examiner* — Susan Hanley
*Assistant Examiner* — Damon B Bowe
(74) *Attorney, Agent, or Firm* — Lowe Hauptman & Ham, LLP

(57) ABSTRACT

Provided are a method of preparing a zinc oxide nanostructure electrode and a method of preparing a dye-sensitized solar cell using the same.
The present invention relates to a use of nicotinic acid adenine dinucleotide phosphate or a derivative thereof for promoting the differentiation of keratinocytes into fibroblasts. The present invention provides a pharmaceutical or cosmetic use of a composition containing NAADP or a derivative thereof for regenerating and improving a skin barrier, or preventing, improving or treating stratum corneum disorders such as psoriasis or atopy, and a use for promoting the differentiation of separated keratinocytes.

6 Claims, 2 Drawing Sheets

(56) References Cited

OTHER PUBLICATIONS

Galione et al. (Biology of the Cell, vol. 92, No. 3-4, p. 197-204, 2000).*
Liu et al.(Marine drugs, vol. 11, No. 6, p. 1899-1908, 2013).*
Uitto et al., Journal of Investigative Dermatology, vol. 132, No. 3, part. 2, p. 820-828, 2012.*
Kit, The Free Dictionary, access Dec. 3, 2013.*
Robert Aarhus et al., ADP-ribosyl Cyclase and CD38 Catalyze the Synthesis of a Calcium-mobilizing Metabolite from NADP, Journal, Dec. 22, 1995, pp. 30327-30333, vol. 270, No. 51, The Journal of Biological Chemistry, The American Society for Biochemistry and Molecular Biology, Inc.
Georgina Berridge et al., Metabolism of the novel Ca2+-mobilizing messenger nicotinic acid-adenine dinucleotide phosphate via a 2'-specific Ca2+-dependent phosphoatase, Article, 2002, pp. 295-301, Biochemical Society.
Eduardo N. Chini et al., CD38 is the major enzyme responsible for synthesis of nicotinic acid-adenine dinucleotide phosphate in mammalian tissues, Article, 2002, pp. 125-130, Biochemical Society.
J.C. Prinz, Which T cells cause psoriasis?, Review article, 1999, pp. 291-295, 24, Blackwell Science Ltd.
Anthony V. Rawlings et al., Stratum Corneum Moisturization at the Molecular Level, Article, 1994, pp. 731-740, Dermatology Foundation.
Peter M. Elias M.D., Epidermal Lipids, Barrier Function, and Desquamation, Article, Jun. 1983, pp. 44s-49s, vol. 80, No. 6.
Roser Masgrau et al., NAADP: A New Second Messenger for Glucose-Induced Ca2+ Responses in Clonal Pancreatic B cells, Article, Feb. 4, 2003, pp. 247-251, vol. 13, Elsevier Science Ltd.
S. Hammer et al., Glucocorticoids Mediate Differential Anti-Apoptotic Effects in Human Fibroblasts and Keratinocytes via Sphingosine-1-Phosphate Formation, Journal, 2004, pp. 840-851, Wiley-Liss, Inc.
Sugato Banerjee et al., CD38/Cyclic ADP-Ribose Regulates Astrocyte Calcium Signaling: Implications for Neuroinflammation and HIV-1-Associated Dementia, Journal, Jun. 26, 2008, pp. 154-164, Springer.
Chinese Office Action for application No. 201180039641.2 dated Mar. 11, 2014.
Japanese Office Action for application No. 2013-524042 dated Mar. 18, 2014.
Luigia Santella et al., Nicotinic Acid Adenine Dinucleotide Phosphate-induce Ca2+ Release, The Journal of biological Chemistry, Mar. 24, 2000, vol. 275, No. 12, pp. 8301-8306, USA.
W Gehring, Nicotinic acid/niacinamide and the skin, Journal of Cosmetic Dermatology, 2004, pp. 88-93, vol. 3, Blackwell Publishing Ltd., US.

* cited by examiner

PHARMACEUTICAL OR COSMETIC COMPOSITION CONTAINING NICOTINIC ACID ADENINE DINUCLEOTIDE PHOSPHATE OR DERIVATIVE THEREOF

TECHNICAL FIELD

The present invention disclosed herein relates to a use of nicotinic acid adenine dinucleotide phosphate (NAADP) or a derivative thereof for promoting the differentiation of keratinocytes, and more particularly, to a pharmaceutical or cosmetic use of a composition containing NAADP or a derivative thereof for regenerating and improving a skin barrier, or preventing, improving or treating stratum corneum disorders, such as psoriasis or atopy, and a use for promoting the differentiation of separated keratinocytes.

BACKGROUND ART

The human skin is composed of dermis and epidermis. The dermis mainly synthesizes collagen and other proteins, and is mainly composed of fibroblasts producing a small amount of lipid. In contrast, the epidermis mainly produces lipid and is mainly composed of keratinocytes substantially not synthesizing collagen. In particular, the epidermis located at the outermost layer of the skin acts to defend against various stimulus form the outside, e.g., physicochemical stimulation factors, such as chemical substances, air pollutants, dry environment, and ultraviolet ray, and to perform a protective function of preventing excessive dissipation of moisture in the body through the skin. Such protective function may be possible by allowing stratum corneum composed of keratinocytes to be normally formed and maintained.

Stratum corneum (homey layer) existing at the outermost layer of the epidermis is formed from keratinocytes and is composed of keratinocytes having differentiation completed and a lipid layer surrounding the keratinocytes (J. Invest. Dermatol. 1983; 80: 44-49). The keratinocytes are cells formed through such a manner that base cells continuously multiplying in stratum basale are subjected to step by step morphological and functional changes while moving to stratum corneum. When a predetermined period of time is elapsed, old keratinocytes are detached from the skin and new keratinocytes moved upward from the stratum basale may substitute the function thereof, and this repetitive process of series of changes is referred to as "epidermis differentiation" or "keratinization". In the process of keratinization, the keratinocytes form the stratum corneum while producing a natural moisturizing factor (NMF) and intercellular lipids (ceramide, cholesterol, and fatty acid) to allow the stratum corneum to have firmless and flexibility, and thus, the stratum corneum may have a function as a skin barrier that acts as an external barrier layer.

The stratum corneum may easily lose its function due to lifestyle factors such as excessive cleansing or bath, environmental factors such as dry air or pollutants, and endogenous diseases such as atopic skin or geriatric skin. In fact, hazard factors on the skin have been gradually increased in modern times, and there is a tendency for a number of people having skin, in which keratinocytes do not exhibit a normal skin barrier function, to be increased according to the fact that generation and detachment rates are decreased due to the changes in dietary habits, and the moisturizing factor and the amount of lipid in the stratum corneum are decreased due to the degradation of the function of the keratinocytes.

It has been revealed that abnormalities in the skin barrier function are the most important cause of xeroderma, regarded as one of the main diseases of modern society. Psoriasis is an inflammatory disease of the skin that is characterized by epidermal proliferation and skin inflammation, in which the skin thickens and turns red due to inflammation and scales (dead skin cells) may occur. Although it is not infectious, it looks ugly, and as a result, patients suffer from stress and degradation of quality of life. Overgrowth and inhibition of differentiation of keratinocytes (Roenigk H H, Marcel Dekker Inc., pp. 233-247, 1985), and abnormalities in the immune system associated with white blood cells, such as T cells or dendritic cells, (J. C. Prinz, Clinical and Experimental Dermatology, 24, 291-295, 1999) have been proposed as causes of the onset of psoriasis. Atopic dermatitis that recently occurs in 10% of children is a chronic recurrent eczematous disease and pathogenesis thereof is not clear. However, the main symptoms thereof include chronic xeroderma and resulting damage to the skin barrier, and if without proper care, atopic dermatitis may develop into lesions such as lichenification, pigmentary changes, and erythroderma. Also, a phenomenon of skin atrophy, occurring in the case of using steroids excessively or over a prolonged period of time, is a side effect in which the skin becomes thinner and the functions thereof are weakened, and it has been reported that the main causes thereof include an inhibition of fibroblast activity and a decrease in the generation of collagen due to steroids (S. Hammer et. al., J. Cell. Biochem, 91, 840-851, 2004).

Typically, for this purpose, a method of increasing moisture retention in the stratum corneum has been performed by using humectants having moisture absorbing properties or occlusive moisturizers preventing evaporation of moisture. Examples of the humectants may be glycerin, propylene glycol, 1,3-butylene glycol, polyethylene glycol, sorbitol, and sodium 2-pyrrolidone-5-carboxylate. However, there may be severe stickiness or may be pultaceous when being applied to the skin. Lipid components, such as ceramide, or essential fatty acids and lipid complexes have been used as occlusive moisturizers (J. Invest. Dermatol. (5), 731-740, 1994), but it may be difficult to maintain stability of emulsified formulations and may not be suitable for preparing transparent gel products. Also, in the case that the foregoing moisturizers having typical moisture retention functions are used, temporary relief of symptoms may be anticipated, but fundamental healing may be difficult. Therefore, there is an urgent need to develop a material fundamentally regenerating the damaged barrier by promoting the differentiation of keratinocytes and the growth of fibroblasts.

Meanwhile, as claims, in which the differentiation of keratinocytes is important to prevent drying of moisture in the skin, have recently been raised, it was found that stratum corneum may play a role as a moisture retention barrier of the skin when a process of differentiation, in which keratinocytes of stratum basale develop into keratinocytes of the outermost stratum corneum, must be normally performed. That is, cells may generate a natural moisturizing factor (NMF) and intercellular lipids during the process of keratinization. As a result, the stratum corneum becomes firm and flexible, and thus, may function as a protective barrier. When physiologically considering the tendency in which the skin dries as the age of a person increases, it may be interpreted that time required for the detachment of stratum corneum is increased or ability of epidermal cells for synthesizing lipids is decreased, and the moisturizing factor and the amount of lipids in the stratum corneum are decreased. Therefore, a new approach able to improve functions of moisture retention and protection from the external environment may be possible by inducing the strengthening of the skin barrier through the promotion of the differentiation of keratinocytes.

DISCLOSURE

Technical Problem

The present invention provides compositions of medicines or functional cosmetics for fundamentally preventing, improving or treating skin diseases and disorders through generation and strengthening of a damaged skin barrier, and methods of preventing, improving or treating the diseases and disorders using the same.

The present invention also provides a composition for promoting differentiation of keratinocytes and a method of promoting the differentiation of keratinocytes.

Technical Solution

In accordance with an exemplary embodiment of the present invention, a composition including nicotinic acid adenine dinucleotide phosphate (NAADP) expressed as Chemical Formula 1 or a derivative thereof as an active ingredient and a method using the same are provided:

[Chemical Formula 1]

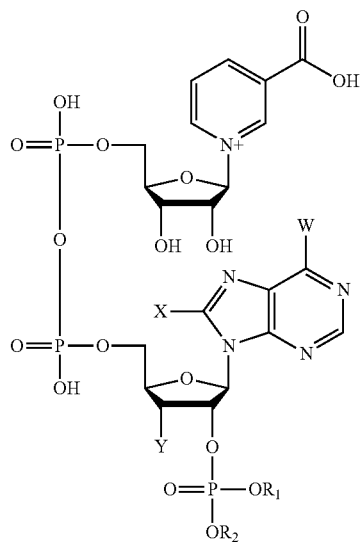

where, $R_1$ and $R_2$ are each independently H, $C_{1-4}$ alkyl (may be unsubstituted or substituted with halogen), or $CH_2$—CO—$CH_3$;

W is selected from the group consisting of $NH_2$, OH, and SH;

X is selected from the group consisting of OH, SH, $NH_2$, and halogen; and

Y is selected from the group consisting of OH, H, $NH_2$, and halogen.

NAADP used in the present invention is synthesized by ADP-ribosyl cyclase including CD38 in cells (Chini E N. et al., Biochem. J., 362: 125-130, 2002; BERRIDGE G. et al., Biochem. J., 365: 295-301, 2002; Aarhus R. et al., J. Bio Chem., 270(51): 30327-30333, 1995), and is important for maintaining the life phenomena of cells, as a material used in controlling a concentration of calcium in the cells of all life forms.

The present inventors found for the first time in the world that NAAP has a function of improving the differentiation potential of keratinocytes during performing research related to the differentiation by treating human normal primary keratinocytes with NAADP. Specifically, the present inventors found that NAADP promotes intracellular calcium release as calcium signaling molecules in the keratinocytes (FIG. 1), and has an effect of increasing expression of involucrin, keratin 1, and keratin 10, differentiation markers of the keratinocytes (FIG. 2). Further, the present inventors obtained the results that NAADP may strengthen the skin barrier by preparing a topical formulation containing NAADP and applying it to the skins of animals and humans (FIG. 3), thereby leading to completion of the present invention.

Hereinafter, the present invention will be described in detail.

The present invention provides a composition for promoting the differentiation of keratinocytes including NAADP expressed as Chemical Formula 1 or a derivative thereof as an active ingredient.

Also, the present invention provides a composition for regenerating and strengthening a skin barrier including NAADP expressed as Chemical Formula 1 or a derivative thereof as an active ingredient.

The composition of the present invention including NAADP expressed as Chemical Formula 1 or a derivative thereof as an active ingredient promotes the differentiation of keratinocytes to regenerate and strengthen the skin barrier, and thus, may be effectively used in preventing or treating skin diseases and disorders such as chronic skin barrier damage diseases, such as psoriasis, atopic dermatitis, and ichthyosis, contact dermatitis, such as primary contact dermatitis and allergic contact dermatitis, acute skin barrier damage diseases, such as allergic dermatitis, xeroderma, eczema, skin atrophy due to steroid side effects, skin wounds, scars, wrinkles, skin aging, generation of age spots, and weakening of skin resilience. However, the present invention is not limited thereto. In the foregoing skin diseases, xeroderma is not limited to the one due to skin aging and environmental causes, and may include the case due to other causes of disease such as hereditary diseases, for example, diabetes, myxedema, lymphoma, tumors, acquired immune deficiency syndrome, and down syndrome, and xeroderma due to zinc deficiency and taking of diuretic or antihistamine. Scars generated in the damaged skin remain more severely when getting older, and this is due to the decline of regenerative ability of the skin. When the regenerative ability of the skin declines, recovery of scars may be delayed and a decrease in skin resilience may be intensified, and thus, the composition of the present invention may improve such limitations by increasing the regeneration of the skin. Also, a natural moisturizing factor (NMF) playing an important role in moisturizing the skin is included in the stratum corneum and it is known that such natural moisturizing factor is produced in the final differentiation process of keratinocytes. Therefore, in the composition of the present invention including NAADP expressed as Chemical Formula 1 or a derivative thereof as an active ingredient, an ingredient promoting the differentiation of keratinocytes may function as a moisturizer by promoting the generation of NMF in addition to promote the mechanism regenerating the skin barrier.

It is to be understood that NAADP or a derivative thereof used in the present invention may not only be provided as a released material, but may also be provided as a pharmaceutically acceptable salt, pharmaceutically acceptable solvate, pharmaceutically acceptable polymorph, or pharmaceutically acceptable prodrug thereof. Also, the active ingredient may be used alone or may also be in the form of conjugates or aggregates with other pharmaceutically active compounds.

The salt of the compound according to the present invention is not particularly limited so long as it has a form able to be formulated in medicines or cosmetics. The salt may include an inorganic salt or organic salt, and may be an acid salt or alkaline salt. In particular, with respect to a salt formed by a cation, the salt may be an alkaline metal salt, such as a sodium salt or potassium salt; an alkaline earth metal salt, such as a calcium salt, a magnesium salt, and a barium salt; a basic amino acid salt, such as arginine or lysine; an ammonium salt such as a tricyclohexyl ammonium salt; and various alkanol amine salts such as a monoethanol amine salt, a diethanol amine salt, a triethanol amine salt, a monoisopropanol amine salt, a diisopropanol amine salt, and a triisopropanol amine salt. The salt may be an alkaline metal salt and for example, may be a tetra sodium salt.

The present invention provides a pharmaceutical composition for promoting the differentiation of keratinocytes including NAADP expressed as Chemical Formula 1 or a derivative thereof as an active ingredient. Also, the present invention provides a pharmaceutical composition for regenerating and strengthening a skin bather including NAADP expressed as Chemical Formula 1 or a derivative thereof as an active ingredient. The present invention also provides a pharmaceutical preparation, particularly a skin external preparation, for treating skin disorders and diseases including an effective amount of the composition.

Further, the present invention provides a method of preventing, treating, or improving the skin disorders and diseases by administering the composition or the preparation into mammals.

The pharmaceutical composition of the present invention including NAADP or a derivative thereof may further include an appropriate carrier, an excipient, and a diluent which are typically used in the preparation of a pharmaceutical composition.

When preparing a preparation, the preparation is prepared by using an excipient, such as a filler, an extender, a binder, a wetting agent, a disintegrant, and a surfactant, or a diluent. An anti-coagulant, a lubricant, a flavouring agent, an emulsifier, and an antiseptic may be further included, and the pharmaceutical composition may be formulated by using a method well known in the art in order to provide rapid, sustained, or delayed release of an active ingredient after being administered into mammals.

The pharmaceutical composition of the present invention including NAADP or a derivative thereof may be prepared as typical pharmaceutical formulations known in the art to which the present invention pertains. The formulations include topical application preparations (topical coating, patch, and iontophoresis), oral administration preparations, injections, suppositories, transdermal preparations, nasal administration preparations, and inhalation preparations, and may be administered by being prepared as a random formulation. However, the pharmaceutical composition of the present invention may be prepared as a transdermal preparation and a skin external preparation for topical application.

In an exemplary embodiment, the composition of the present invention is a skin external preparation and may be prepared as all formulations applicable to the skin, such as a solution, a suspension, an emulsion, ointment, paste, gel, cream, lotion, powder, spray, a pack, a skin adhesive patch, a dressing, a hydrous adhesive patch, or an anhydrous adhesive patch.

In the case that the formulation of the present invention is paste, cream, or gel, animal oil, vegetable oil, wax, paraffin, starch, tragacanth, a cellulose derivative, polyethylene glycol, silicon, bentonite, silica, talc, or zinc oxide may be used as a carrier component.

In the case that the formulation of the present invention is powder or spray, lactose, talc, silica, aluminum hydroxide, calcium silicate, or polyamide powder may be used as a carrier component, and particularly, with respect to spray, propellants, such as chlorofluorohydrocarbon, propane/butane, or dimethyl ether, may be additionally included.

In the case that the formulation of the present invention is a solution or an emulsion, a solvent, a solubilization agent, or an emulsifying agent is used as a carrier component, and for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or sorbitan fatty acid ester may be used.

In the case that the formulation of the present invention is a suspension, a liquid diluent such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, or tragacanth may be used as a carrier component.

Also, application amounts of various known ingredients formulated in cosmetics applied to the skin or the mucosal, or topical drugs•quasi-drugs may be formulated in the skin external preparation of the present invention.

These ingredients include a flavouring agent, a coloring (dye, pigment), a chelating agent, a deodorant, a film former, an ultraviolet absorber, an ultraviolet scattering agent, and vitamins, in addition to an antioxidant (e.g., carboxylic acids such as ascorbic acid and citric acid; and phenols such as tocopherol and dibutyl hydroxy toluene), an antiseptic (e.g., carboxylic acids such as dehydroacetic acid, salicylic acid, edentate disodium; and phenols such as paraoxybenzoic acid ethyl, paraoxybenzoic acid methyl, paraoxybenzoic acid isopropyl, and thymol), a wetting agent (e.g., glycols such as glycerin, propylene glycol, dipropylene glycol, 1,3-butylene glycol; organic salts such as hyaluronic acid; and amides such as urea), a viscosity increasing agent (e.g., polymer compounds such as polyethylene glycol; and celluloses such as sodium carboxymethyl cellulose, carboxypropyl cellulose), a buffer (e.g., organic acids such as citric acid, lactic acid, and tartaric acid; inorganic acids such as hydrochloric acid and boric acid; salts such as sodium dihydrogen phosphate and sodium citrate; organic salts such as triethanolamine; and inorganic bases such as sodium hydroxide and potassium hydroxide), an absorbent (e.g., hydrous aluminum silicates such as kaoline and bentonite; and inorganic salts such as alumina magnesium hydroxide and aluminum hydroxide), a base (e.g., organics such as white Vaseline, Tween 60, Tween 80, liquid paraffin, wax, Vaseline, castor oil, silicon oil, hydrogenated castor oil, natural rubber, palm oil fatty acid diethanolamide, polyoxyethylene hydrogenated castor oil, natural rubber latex, and a 1,3-pentadien copolymer resin; polymer compounds such as polybutene, synthetic rubber styrene butadiene rubber (SBR), mono-stearic acid polyethylene glycol, mono-stearic acid polyoxyethylene glycol, polyoxyethylene cetostearyl ether, polyoxyethylene oleyl cetyl ether, silicon, acrylic acid starch 300, sodium polyacrylate, methacrylic acid•acrylic acid n-butyl copolymer, and carboxyvinyl polymer; fatty acids such as stearic acid; alcohols such as cetanol and myristyl alcohol; and fatty acid esters such as myristic acid octadodecyl, myristic acid isopropyl, and cetyl octanoate), a solvent (e.g., carbohydrates such as ethanol, isopropanol, 1,3-butylene glycol, n-octadecyl alcohol, crotamiton, and tri(caprylic acid•capron)glycerin), a stabilizer (e.g., inorganic salts such as sodium metaphosphate, zinc oxide, and titanium oxide; and organic salts such as polyoxyethylene lauryl ether sodium sulfate and sodium lauryl sulfate), an adhesive (e.g., polymers such as sodium polyacrylate and dipropylene glycol), an emulsifier (e.g., carbohydrates such as monoolefinic acid sorbitan, monoolefinic acid polyoxyethylene sorbitan, D-sorbitol, polyglycerin monolaurate, and polyoxyethylene lauryl ether sodium sulfate), and a surfactant (e.g., polymers such as polyglycerin monolaurate and polyoxyethylene oleyl alcohol ether).

Also, the composition used as a skin external preparation may further include a skin absorption promoting material in order to increase an effect of strengthening a skin barrier function, an effect of inducing the differentiation of keratinocytes, and an effect of moisturizing the skin.

Further, in preparing the skin external preparation of the present invention, other active ingredients may be included so long as these active ingredients do not inhibit the pharmacological effects thereof. For example, these active ingredients may be a known refreshing ingredient, a sebum inhibitor, an antiseborrheic agent, a germicide, an anti-inflammatory, a skin astringent, a cell activator, a vasodilator, a blood circulation stimulant, a skin function agonist, and a crude drug. Specifically, examples of the active ingredients may be menthol, salicylic acid, estradiol, glycyrrhizic acid, benzalkonium chloride, phenol, camphor; narcotics and stimulants such as ethylmorphine hydrochloride, oxycodone hydrochloride, cocaine hydrochloride, pethidine hydrochloride, methamphetamine hydrochloride, dl-methylephedrine hydrochloride, morphine hydrochloride, fentanyl citrate, and levallorphan tartrate; a topical disinfectant such as povidone iodine and iodoform; an enzyme preparation such as lysozyme chloride, streptokinase, streptodornase, trypsin, and deoxyribonuclease; and crude drugs such as a lithospermum erythrorhizon root extract and a scopolia extract.

An aqueous suspension may contain fine particles of an active ingredient with one or more suspending agents such as sodium carboxymethyl cellulose, methyl cellulose, hydroxypropyl methyl cellulose, sodium alginate, polyvinyl-pyrrolidone, gum tragacanth, and gum acacia; dispersants or wetting agents such as lecithin or condensation products of alkylene oxide with fatty acids (e.g., polyoxyethylene stearate), or condensation products of ethylene oxide with long-chain aliphatic alcohols such as heptadeca-ethyleneoxy-cetanol, or condensation products of ethylene oxide with partial esters derived from fatty acids and a hexitol, such as polyoxyethylene sorbitol monooleate, or condensation products of ethylene oxide with partial esters derived from fatty acids and hexitol anhydrides, such as polyoxyethylene sorbitan monooleate. The aqueous suspension may also contain one or more preservatives (e.g., ethyl, or propyl-p-hydroxy benzoate), an antioxidant (e.g., ascorbic acid), a coloring agent, a fragrance, and/or a sweetening agent (e.g., sucrose, saccharin, or aspartame).

An oily suspension may be formulated by suspending an active ingredient in vegetable oil (e.g., arachis oil, olive oil, sesame oil, or coconut oil) or mineral oil (e.g., liquid paraffin). The oily suspension may also contain a thickener such as wax, light paraffin, or cetyl alcohol. An oral preparation having good taste may be provided by adding the foregoing sweetening agent and fragrance. These compositions may be preserved by adding antioxidants such as ascorbic acid.

Dispersible powder and granule suitable for preparing an aqueous suspension by adding water may generally contain an active ingredient with a dispersant or wetting agent, a suspending agent, and one or more preservatives. The suitable dispersant or wetting agent and the suspending agent may be exemplified by the foregoing. Additional excipients, such as a sweetening agent, a fragrance, and a coloring agent, may also be included.

The pharmaceutical composition of the present invention may also have the form of an oil-in-water type emulsion. An oil phase may be vegetable oil such as olive oil or arachis oil, or mineral oil such as liquid paraffin, or a mixture of random oils thereof. Examples of a suitable emulsifier may be naturally occurring gums, such as gum acacia or gum tragacanth, naturally occurring posphatides, such as esters or partial esters derived from soybeans, lecitine, fatty acids, and hexitol anhydrides (e.g., sorbitan monooleate), and condensation products of ethylene oxide with the partial esters, such as polyoxyethylene sorbitan monooleate. The emulsion may also contain a sweetening agent, a fragrance, and a preservative.

Syrup and elixir may be formulated by using a sweetening agent, such as glycerol, propylene glycol, sorbitol, aspartame, or sucrose, and may also contain a demulcent, a preservative, a fragrance, and/or a coloring agent.

Appropriate amount and time of administration of the composition of the present invention may be different from methods of preparation and age, sex, weight, degree of disease symptom, excretion rate and reaction sensitivity, and administration route and duration of a target of administration, but an effective amount of administration for the treatment known to those skilled in the art may be appropriately selected. For example, with respect to a preparation for oral administration, the composition may be administered a few times a day by randomly dividing the amount of administration to be in a range of 0.01 g/kg to 10.0 g/kg, for example, 0.1 g/kg to 1.0 g/kg based on the adult. Also, with respect to a skin external preparation, the effective amount may be applied in a range of 1 nM to 10 mM, for example, 1 nM to 100 µM per a skin surface area ($cm^2$) for a day, in which the amount may be applied one to five times a day. A dose formulation of the composition may be a single-dose formulation or a multiple-dose formulation, and the composition may be administered a few times a day by randomly dividing the effective amount.

The pharmaceutical composition of the present invention may be used in monotheraphy, but may be used in combination with surgery, hormone therapy, radiation therapy, drug treatment, a method of using a biological response modifier, and diet.

The composition of the present invention may further include cells constituting the skin, such as keratynocytes, in addition to NAADP of Chemical Formula 1 or a derivative thereof.

In an additional aspect of the present invention, the present invention provides a functional cosmetic composition for improving a skin barrier function and moisturizing skin including NAADP of Chemical Formula 1 or a derivative thereof. The composition of the present invention may recover the skin bather function by promoting the differentiation of keratynocytes, and thus, may increase a protective function against the external environment and may prevent or improve skin disorders or diseases such as skin wounds, scars, wrinkles, loss of resilience or atopic dermatitis, eczema, or psoriasis. Also, the composition of the present invention may have an effect of relieving strain of the skin and roughness, and increasing radiance by improving the moisture retention function of the skin.

Functional cosmetics of the present invention containing NAADP of the present invention or a derivative thereof as an active ingredient may be applied to all formulations applied to the skin. More particularly, the functional cosmetics may be prepared in cleansing foam, cleansing cream, body lotion, body cream, body oil, body cleanser, soap, shampoo, ointment, and a patch as well as cosmetics, such as toner, lotion, gel, cream, essence, water-soluble powder, fat-soluble powder, water-soluble liquid, foundation, spray, and a pack. In addition, the functional cosmetics may be prepared as a skin contact material contacting the skin, such as makeup, detergent, and fibers.

In the cosmetic composition of each formulation, other ingredients in addition to NAADP or a derivative thereof may be appropriately selected and formulated by those skilled in the art within the scope of not impairing the purpose and effect of the present invention. Examples of the formulation ingredients able to be added may be a fat ingredient, a moisturizer, an emollient, a surfactant, organic and inorganic pigments, organic powder, an ultraviolet absorber, an antiseptic, a germicide, an antioxidant, a plant extract, a pH regulator, alcohol, a coloring, a flavouring agent, a blood circulation stimulant, a cooling agent, an adiaphoretic agent, and purified water.

Also, the cosmetics of the present invention may further include ingredients selected from the group consisting of water-soluble vitamin, oil-soluble vitamin, polymer peptide, polymer polysaccharide, sphingolipid, and a seaweed extract, in addition to NAADP or a derivative thereof.

The cosmetic composition of the present invention may be used by applying an appropriate amount to the skin according to a skin area to be applied and may be repeatedly used one to a few times a day as needed. The amount and number of the application may be changed as needed according to skin condition and age of an individual.

In another aspect of the present invention, the present invention provides a method of promoting the differentiation of keratinocytes including an operation of contacting a culture of stratum corneum or keratinocytes of the skin with the composition in vivo, ex vivo, and in vitro.

The culture of keratinocytes may not only be widely used for treating skin damages such as burn, chronic diseases, and vitiligo, but may also be used for researching differentiation stages of the cell. In order to medically use keratinocytes, there is a need to massively multiply the keratinocytes from a small amount of cells obtained from the human body in a culture vessel.

In an exemplary embodiment, the method includes an operation of contacting keratinocytes separated from mammals or keratinocytes separated from mammals and cultured with the composition including NAADP of Chemical Formula 1 or a derivative thereof. The differentiated cells obtained by the method may be used in experiments in vivo or in vitro, and may be used in injections and transplants for transplantation for tissue repair/regeneration, and artificial skin, but the present invention is not limited thereto. The method may further include an operation of applying an effective amount of the composition according to the present invention to the skin of an individual mammal requiring regeneration and differentiation of the epidermis. The effective amount of the composition, and the number, interval, and period of application may be appropriately selected by those skilled in the art according to the purpose thereof.

The present invention also provides a kit including NAADP of Chemical Formula 1 or a derivative thereof that is used for the purpose of promoting the differentiation of keratinocytes.

In another aspect, the present invention provides a method of using the composition for preparing a medicine for treating the skin diseases and disorders.

In another aspect of the present invention, the present invention provides a method of screening a material able to adjust differentiation potential of keratinocytes of a subject material having the composition of the present invention used therein. The method includes, preparing separated human keratinocytes;

contacting the separated human keratinocytes respectively with a composition containing NAADP or a derivative thereof and a subject material;

detecting increased amounts of calcium or expression levels of a differentiation marker in the keratinocytes; and comparing the increased amounts of calcium or the expression levels of the differentiation marker detected in the keratinocytes contacted with the composition and the subject material to determine ability of the subject material to induce differentiation of keratinocytes.

Any cell may be used as the human keratinocytes used in the screening method so long as changes in calcium and the expression levels of the differentiation marker may be distinguished by being cultured respectively under the existences of the composition of the present invention and the subject material. Human foreskin derived normal cells and a cultured cell system formed of epidermal keratinocyte neonatal (NHEK-Np, CC-2507, Lonza Co. Ltd.) as a feeder layer may be appropriately used.

Specific proteins, such as involucrin, loricrin, keratin 1, or keratin 10, may be used as a differentiation marker of keratinocytes, but the present invention is not limited thereto. The presence and amount of expression may be measured by using a typical method of detecting proteins such as western blot.

The increased amount of calcium or the expression level of a differentiation marker is detected by using a known measurement method and thus, the ability to induce differentiation of keratinocytes by the subject material, and further, a degree of efficacy in regenerating and strengthening a skin barrier may be evaluated.

Advantageous Effects

A composition of the present invention including nicotinic acid adenine dinucleotide phosphate (NAADP) or a derivative thereof exhibits effects of recovering a damaged skin bather function and increasing skin hydration through the promotion of the differentiation of keratinocytes. Therefore, the composition including NAADP or a derivative thereof may be used as a pharmaceutical composition or a functional cosmetic composition for regenerating and strengthening a skin bather and moisturizing skin, and may be used as a material for inducing the differentiation of keratinocytes in vitro. Also, medicines or cosmetics including the composition may be effectively used for preventing or treating skin diseases and disorders such as chronic skin barrier damage diseases such as psoriasis, atopic dermatitis, and ichthyosis, contact dermatitis such as primary contact dermatitis and allergic contact dermatitis, acute skin barrier damage diseases such as allergic dermatitis, xeroderma, eczema, skin atrophy due to steroid side effects, skin wounds, scars, wrinkles, skin aging, generation of age spots, and weakening of skin resilience.

BEST MODE

Hereinafter, the present invention will be described in more detail according to examples. However, the examples are merely presented to exemplify the present invention, and the scope of the present invention is not limited thereto.

EXAMPLE 1

Verification of Effect of NAADP on Increasing Calcium in Keratinocytes

Normally, since a calcium gradient exists in epidermis, a concentration of calcium ions is low in stratum basale and stratum spinosum, and increases as approaching to an upper layer, and thus, the concentration is the highest in external stratum granulosum. Damage of a skin barrier induces a loss of moisture from an upper portion of the skin and the resultant loss of moisture causes changes in the calcium gradient in the epidermis. The changes in the calcium gradient induce recovery of homeostasis in the skin and as a result, a skin barrier function is rapidly recovered and subsequently, the calcium gradient having a normal configuration may be formed. That is, it was revealed that the changes of calcium ions may play an important role as a signal of starting a process of recovery after the damage of the skin barrier.

In the present example, an efficacy in inducing an increase in intracellular calcium was evaluated when cultured keratinocytes were treated with NAADP in order to confirm an effect of recovering a skin barrier in the composition of the present invention.

Method

Figure 1:
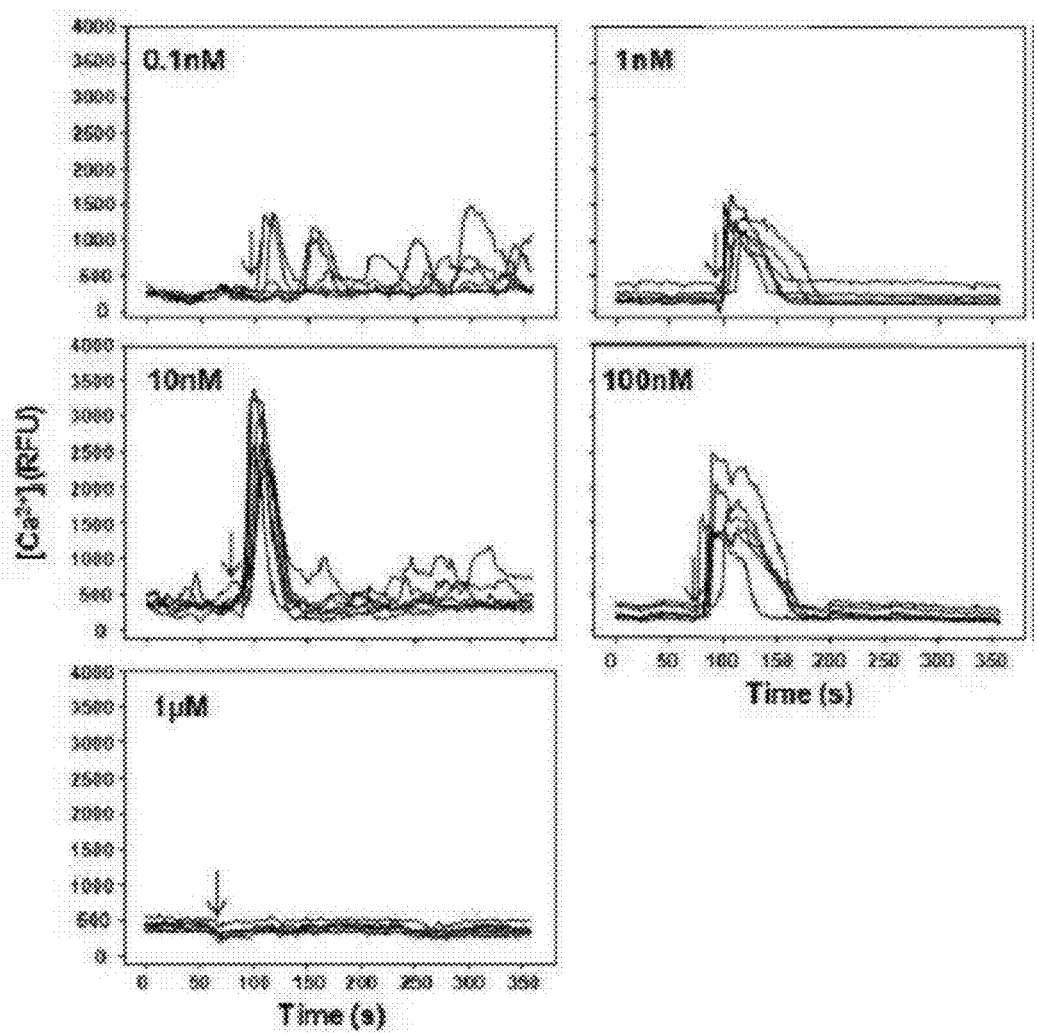
FIG. 1 is a graph illustrating effects of a composition including nicotinic acid adenine dinucleotide phosphate (NAADP) on changes in the concentration of calcium in primarily cultured keratinocytes for each concentration.

Epidermal keratinocyte neonatal (NHEK-Np, CC-2507, Lonza Co. Ltd.) was treated with fluo-3 AM (Molecular Probe, USA), an intracellular calcium marker, for 30 minutes in a $CO_2$ incubator and then washed with a KBM (Keratinocyte Basal Media, KBM-2, Lonza Co. Ltd.) medium three times. Measurement of intracellular calcium was performed in the KBM medium and an increase in intracellular calcium due to NAADP was observed. For the measurement of intracellular calcium, a concentration of calcium was calculated through the collection of images at 530 nm by using a confocal microscopy (Nikon, Japan) equipped with a laser source having an excitation wavelength of 488 nm and an emission wavelength of 530 nm Amounts of changes in calcium measured when epidermal keratinocyte neonatal ($5 \times 10^5$ cells) was treated with 0.1 nM, 1 nM, 10 nM, 100 nM, 1000 nM of NAADP are illustrated in FIG. 1, respectively.

Results

It was confirmed that movement of intracellular calcium was induced during the treatment of the epidermal keratinocyte neonatal with 1 nM to 100 nM of NAADP. In terms of the fact that calcium acts as an important signaling molecules in a damaged skin barrier, it was confirmed that the composition containing NAADP in the present invention exhibited fast recovery effect on the skin barrier function. Such results, along with the results of the induction of the differentiation of epidermal keratinocyte neonatal performed below, indicated that the composition had effects on wound healing, atopic dermatitis, psoriasis, eczema, and skin aging.

EXAMPLE 2

Verification of Efficacy of NAADP in Promoting Differentiation of Keratinocytes

Keratinocytes are cells playing a very important role in moisturizing and protecting skin by forming the outermost layer of the skin, in which excessive proliferation may be inhibited, apoptosis may be inhibited, and differentiation may be promoted. The excessive proliferation may become a cause of rough and thick skin by the abnormally enlargement of the keratinocytes and a normal skin barrier function may not be performed due to abnormal differentiation, and thus, the possibility of causing various diseases, such as xeroderma, atopic dermatitis, and psoriasis, may be increased.

An effect of NAADP on promoting cell differentiation was tested by measuring the expression of differentiation markers (involucrin, keratin 1, and keratin 10) generated during the differentiation of the keratinocytes by using a western blotting method.

Method

Primarily cultured epidermal keratinocyte neonatal was put into a culture flask and attached to the bottom thereof, and then cultured for 5 days until the cells grew to cover about 70% to 80% of an area of the bottom by adding NAADP diluted for each concentration and retinol acid as a control group into a culture medium. The cells were harvested and cleaned with phosphate buffered saline (PBS). Next, precipitates obtained by adding 1 ml of a 10 mM tris-HCl (pH 7.4) buffer solution containing 2% sodium dodecyl sulfate (SDS) and 20 mM dithiothreitol (DTT) and being subjected to sonication, boiling, and centrifugation were again suspended in 1 ml of PBS. A content of protein in the suspension was measured and used as a criterion during the evaluation of a degree of cell differentiation. The results of tests performed by using a group treating the epidermal keratinocyte neonatal ($5 \times 10^5$ cells) with retinol acid (1 μM) as a positive control group and adding each NAADP having different concentration (10 pM to 10 μM) to a low calcium concentration are presented in the following FIG. 2.

Results

Figure 2:
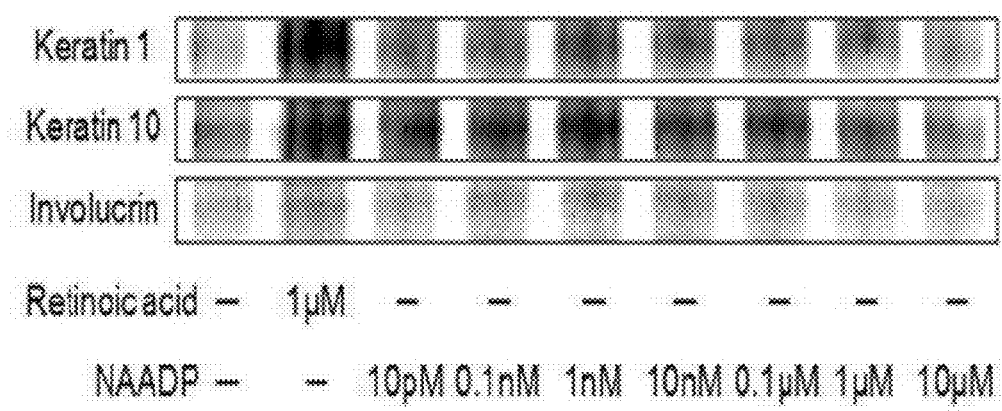
FIG. 2 is western blot photographs, in which effects of the composition including NAADP on the differentiation of primarily cultured keratinocytes are evaluated by using expression levels of involucrin, keratin 1, and keratin 10, differentiation markers.
Figure 3:
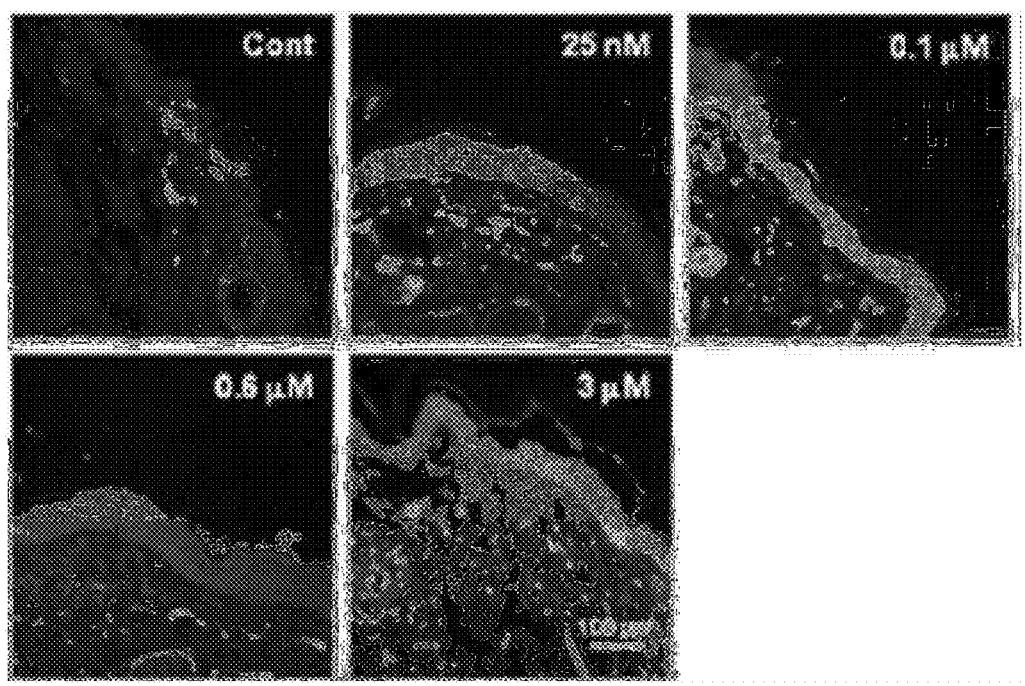
FIG. 3 is photographs showing skin tissues of mice illustrating degrees of inducing the differentiation of stratum corneum according to concentrations when the compositions including NAADP are applied to the hairless mice.

As a result of evaluating the effect on the differentiation of keratinocytes, it may be confirmed that differentiation markers were expressed in a group treated with 10 pM to 10 μM of NAADP as illustrated in FIG. 2, and better effects were expressed with respect to keratin 1 and keratin 10. Therefore, it was confirmed that the foregoing materials had effects of improving the differentiation potential of keratinocytes. Thus, the fact that the composition according to the present invention may promote the differentiation of keratinocytes and as a result, may rapidly recover the skin barrier function was identified.

EXAMPLE 3

Verification of Efficacy of NAADP in Inducing Differentiation of Keratinocytes in Hairless Mouse Hairless mice (SPF/VAF Crl:SKH 1-hr) used in the present tests were purchased from OrientBio (Seongnam, Korea). NAADP, an experiment material of the present invention, used was a product of Sigma-Aldrich Corporation.

Method

Test materials were prepared by dissolving NAADP for each concentration in a solution, in which 1% dimethyl sulfoxide (DMSO) was added to a phosphate buffer solution, and tests were performed by using a method of applying the test materials on right and left portions of the back of a 6-week-old mouse with cotton swabs. The test materials were applied 5 times for each concentration and the applications were performed twice a day at 9:00 a.m. and 7:00 p.m. Animals having the test materials applied for one week were sacrificed by cervical dislocation, and the skin was dissected to prepare a size of 1 cm×1 cm and was then fixed in a 10% formalin solution over a night. A paraffin block was prepared from the fixed tissues to prepare 5 micrometer slices and the slices were dyed with an antibody (Santa Cruz #SC53251) simultaneously identifying keratin 1 and keratin 10 at a dilution ratio of 1:100. Anti-mouse IgG (invitrogen) combined with Alexa 488 was used as a secondary antibody.

A solution, in which 1% DMSO was added to a phosphate buffer solution, was used as a control group and solutions prepared by diluting the solution used as the control group with NAADP in various concentrations were used as a test group.

Results

It may be confirmed that expression levels of keratin 1 and keratin 10 in a portion of outer skin of the NAADP treated group were increased in comparison to those of the control group and it may also be understood that a concentration at which an increase in the expression level of the corresponding differentiation marker appeared was 100 nM or more.

In in vitro tests, calcium was increased and the expression of the markers were decreased by the treatment of NAADP having a high concentration (see Examples 1 and 2), but in the present tests, it was confirmed that keratin 1 and keratin 10 were increased by depending on the concentration of NAADP. The reason for this is considered that there was a difference between processes of being absorbed through a skin barrier in vivo and under a condition of using only animal cells.

PREPARATION EXAMPLES

Preparation Example 1

Topical Cream (100 g)

A moisturizer and NAADP were added to purified water, and then heated and adjusted to 70° C. Oil ingredients were heated and dissolved, and an emulsifier and an antiseptic were then added thereto and the temperature was adjusted to 70° C. The solution thus obtained was added to the prepared water phase and emulsified particles were homogenized with a homomixer, and then deaeration, filtration, and cooling were performed.

Main ingredient NAADP 1.0 mg
Oil ingredient Cetostearyl alcohol 6.0 g
Stearic acid 2.0 g
Lanolin 4.0 g
Squalane 9.0 g
Octyldodecanol 1.0 g
Moisturizer 1,3-butylene glycol 3.0 g
Glycerin 2.0 g
Emulsifier POE (25) cetyl alcohol ether 3.0 g
Glyceryl monostearate 2.0 g
* Antiseptic Propylparaben appropriate amount
Methylparaben appropriate amount
Purified water residual amount Preparation Example 2

Topical Lotion (100 g)

NAADP and a moisturizer were added to purified water, and then heated and adjusted to 70° C. Oil ingredients were heated and dissolved, and an emulsifier and an antiseptic were then added thereto and the temperature was adjusted to 70° C. The solution thus obtained was added to the prepared water phase and emulsified with a homomixer. Thereafter, an aqueous hyaluronic acid 1 solution was added thereto and uniformly mixed with a homomixer, and deaeration, filtration, and cooling were then performed.

Main ingredient NAADP 1.0 mg
Oil ingredient Cetostearyl alcohol 1.0 g
Wax 0.5 g
Vaseline 2.0 g
Squalane 6.0 g
Dimethylpolysiloxane 2.0 g
Emulsifier POE (10) mono-oleic acid ester 1.0 g
Glycerol mono-stearic acid ester 1.0 g
Moisturizer Glycerin 4.0 g
1,3-butylene glycol 4.0 g
* Antiseptic Propylparaben appropriate amount
Methylparaben appropriate amount
Purified water residual amount Preparation Example 3

Gel (100 g)

Polyethylene glycol was added and dissolved in purified water, and NAADP was then added thereto and dissolved by heating. The solution thus obtained was cooled to about 50° C. and a solution, in which polyoxyethylene cetyl ether was added to propylene glycol and glycerin under stirring and heated to about 50° C., was added thereto. Also, sodium hydroxide was added thereto under continuously stirring and a solution was prepared to obtain a pH of about 6.8. After cooling to about 40° C., isopropanol was added thereto, and the solution was cooled to about 25° C. The solution was then collected in an appropriate container.

NAADP 1 mg
Polyethylene glycol 8 g
Carboxyvinyl polymer 0.5 g
Methyl cellulose 0.2 g
Propylene glycol 5 g
Glycerin 2 g
Polyoxyethylene oleyl cetyl ether 1 g
Isopropanol 5 g
Sodium hydroxide appropriate amount
Purified water residual amount Preparation Example 4

Nourishing Cream (100 g)

Nourishing cream was prepared in the same manner as Preparation Example 1 by using the following ingredients.

NAADP 0.5 mg
Stearyl alcohol 6.0 g
Stearic acid 2.0 g
Concentrated Glycerin 1.0 g
Squalane 9.0 g
1,3-butylene glycol 6.0 g Polysorbate 60 1.5 g
Polyethylene glycol 1000 4.0 g
Hydrogenated Lanolin 4.0 g
Octyldodecanol 10.0 g
Sorbitan stearate 0.8 g
Triethanolamine 0.5 g
Antiseptic appropriate amount
Flavouring agent appropriate amount
Coloring appropriate amount
Purified water residual amount

The invention claimed is:

1. A method of strengthening a skin barrier comprising: applying a composition to the skin of a mammal, wherein the composition comprises: a nicotinic acid adenine dinucleotide phosphate (NAADP) expressed as the following Chemical Formula 1, or a pharmaceutically acceptable salt, pharmaceutically acceptable solvate, thereof, as an active ingredient,

[Chemical Formula 1]

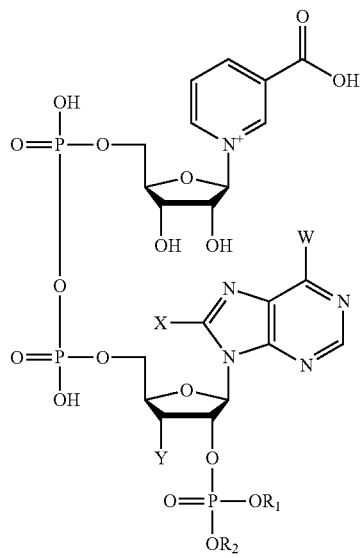

where,

R$_1$ and R$_2$ are each independently H, C$_{1-4}$ alkyl, unsubstituted or substituted with halogen, or CH$_2$—CO—CH$_3$;

W is selected from the group consisting of NH$_2$, OH, and SH;

X is selected from the group consisting of OH, SH, NH$_2$, and halogen; and,

Y is selected from the group consisting of OH, H, NH$_2$, and halogen.

2. The method of claim 1, wherein the pharmaceutical composition is used for treating skin diseases and disorders including psoriasis, atopic dermatitis, ichthyosis, primary contact dermatitis, allergic contact dermatitis, allergic dermatitis, xeroderma, eczema, skin atrophy due to steroid side effects, skin wounds, scars, wrinkles, skin aging, generation of age spots, or weakening of skin resilience.

3. The method of claim 1, wherein the pharmaceutical composition is formulated as a skin external preparation selected from the group consisting of a solution, a suspension, an emulsion, ointment, gel, paste, cream, lotion, powder, spray, a pack and a skin adhesive patch, a dressing, a hydrous adhesive patch, or an anhydrous adhesive patch.

4. The method of claim 3, wherein, with respect to a skin external preparation, a dose of the active ingredient is in a range of 1 nM to 100 µM per a skin surface area (cm$^2$) for a day.

5. The method of claim 1, wherein applying the composition comprises applying a functional cosmetic composition.

6. A method of promoting differentiation of keratinocytes of mammals, the method comprising contacting keratinocytes separated from skin of mammals and culturing said separated keratinocytes with a composition comprising a nicotinic acid adenine dinucleotide phosphate (NAADP) expressed as the following Chemical Formula 1, or a salt, or a solvate thereof, as an active ingredient,

[Chemical Formula 1]

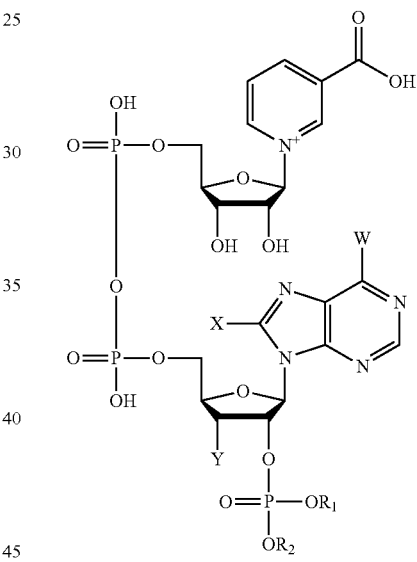

where,

R$_1$ and R$_2$ are each independently H, C$_{1-4}$ alkyl, unsubstituted or substituted with halogen, or CH$_2$—CO—CH$_3$;

W is selected from the group consisting of NH$_2$, OH, and SH;

X is selected from the group consisting of OH, SH, NH$_2$, and halogen; and,

Y is selected from the group consisting of OH, H, NH$_2$, and halogen.

* * * * *